US009958371B2

(12) United States Patent
Blackford et al.

(10) Patent No.: US 9,958,371 B2
(45) Date of Patent: May 1, 2018

(54) COLLOID SIZE DISTRIBUTION MEASUREMENT TECHNOLOGY

(71) Applicant: Fluid Measurement Technologies, Inc., White Bear Lake, MN (US)

(72) Inventors: David Blackford, White Bear Lake, MN (US); Derek Oberreit, Roseville, MN (US); Donald C. Grant, Grand Marais, MN (US); Gary Van Schooneveld, Eden Prairie, MN (US); Mark R. Litchy, Plymouth, MN (US)

(73) Assignee: Fluid Measurement Technologies, Inc., White Bear Lake, MN (US)

( * ) Notice: Subject to any disclaimer, the term of this patent is extended or adjusted under 35 U.S.C. 154(b) by 297 days.

(21) Appl. No.: 14/665,605

(22) Filed: Mar. 23, 2015

(65) Prior Publication Data

US 2015/0308940 A1    Oct. 29, 2015

Related U.S. Application Data

(60) Provisional application No. 61/969,478, filed on Mar. 24, 2014, provisional application No. 62/074,931, filed on Nov. 4, 2014.

(51) Int. Cl.
*G01N 15/02* (2006.01)
*G01N 15/06* (2006.01)
*G01N 15/00* (2006.01)

(52) U.S. Cl.
CPC ..... *G01N 15/0211* (2013.01); *G01N 15/0255* (2013.01); *G01N 15/065* (2013.01);
(Continued)

(58) Field of Classification Search
CPC .......... G01N 15/0211; G01N 15/0255; G01N 15/065; G01N 2015/0053; G01N 2015/0088; G01N 2015/0261
(Continued)

(56) References Cited

U.S. PATENT DOCUMENTS 7,656,510 B2 *   2/2010   Roberts ............. G01N 15/0205
                                                              356/37
8,272,253 B2 *   9/2012   Grant .................. G01N 1/4022
                                                              73/61.72

(Continued)

*Primary Examiner* — Hezron E Williams
*Assistant Examiner* — Marrit Eyassu
(74) *Attorney, Agent, or Firm* — Skinner and Associates; Joel Skinner (57) ABSTRACT

A method and system of measuring the size distribution of particles within dilute colloids, for example, through variation of the minimum detected size of aerosolized colloid particles. The method of determining the size distribution of particles in a fluid, involves forming a stream of aerosol droplets of the fluid, the droplets containing particles and dissolved material, evaporating the droplets to generate particles, and measuring the concentration of particles by varying a detection threshold. A system or apparatus for determining the size distribution of particles in a fluid, includes a droplet former for forming a stream of aerosol droplets of the fluid, the droplets containing particles and dissolved material, and a condensation particle detector for evaporating the droplets to generate particles and for measuring the concentration of particles, the condensation particle detector having a variable detection threshold.

38 Claims, 8 Drawing Sheets

(52) U.S. Cl.
CPC ........... *G01N 2015/0053* (2013.01); *G01N 2015/0088* (2013.01); *G01N 2015/0261* (2013.01)

(58) Field of Classification Search
USPC ...................................... 73/61.71
See application file for complete search history.

(56) References Cited

U.S. PATENT DOCUMENTS

| | | | |
|---|---|---|---|
| 2004/0012772 A1* | 1/2004 | Ahn .............. | G01N 15/065 356/37 |
| 2006/0208098 A1* | 9/2006 | Shdaimah ........ | G01N 5/025 236/44 C |
| 2008/0152547 A1* | 6/2008 | Hopke ............ | B01D 47/05 422/109 |
| 2009/0009749 A1* | 1/2009 | Ahn .............. | G01N 15/065 356/37 |
| 2011/0091649 A1* | 4/2011 | Liu .............. | G01N 15/065 427/255.25 |
| 2011/0214489 A1* | 9/2011 | Grant ............ | G01N 1/4077 73/61.72 |

* cited by examiner

COLLOID SIZE DISTRIBUTION MEASUREMENT TECHNOLOGY

CROSS REFERENCE TO RELATED APPLICATIONS, IF ANY

This application claims the benefit under 35 U.S.C. § 119(e) of U.S. Provisional Patent Application Ser. No. 61/969,478, filed Mar. 24, 2014, and Ser. No. 62/074,931, filed Nov. 4, 2014 which are hereby incorporated by reference.

37 C.F.R. §1.71(E) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

Field of the Invention

The present invention relates, generally, to methods and apparatus for analyzing material. Particularly, the invention relates to methods and apparatus for measuring the size distribution of particles in dilute colloids. Most particularly, the invention relates to methods and apparatus for measuring the size distribution of particles within the dilute colloid through variation of the minimum detected size of aerosolized colloid particles. The technology is useful, for example, for colloid characterization, filter testing, and high purity water system monitoring.

Background Information

Existing technology in this field is believed to have significant limitations and shortcomings. Specifically, systems used to measure particle size distributions in colloids are limited to particle diameters greater than 25 nm, when such colloids are present at very low concentrations in ultrapure liquids.

Small particles are a major problem for the semiconductor device manufacturing industry. Particles smaller than 50 nm can significantly reduce manufacturing yield of present day semiconductor devices. The ability to measure concentrations, especially low concentrations, of these particles is highly desired. A brief summary of the state of the art is provided in U.S. Pat. Nos. 8,272,253 and 8,573,034.

All US patents and patent applications, and all other published documents mentioned anywhere in this application are incorporated by reference in their entirety.

BRIEF SUMMARY OF THE INVENTION

The present invention provides analysis methods and apparatus which are practical, reliable, accurate and efficient, and which are believed to constitute an improvement over the background technology. In the preferred embodiment, the invention relates to an aerosolization apparatus and method which creates fine droplets of the fluid (nebulization) containing particles and dissolved material at concentrations equal to the bulk material. Upon evaporation of the liquid, the gas-borne droplet becomes either a particle consisting of non-volatile dissolved material or a particle consisting of a colloid particle and non-volatile dissolved material. At the residue concentrations and particle sizes of interest, these aerosol particles are too small to be detected optically. The particles are then sampled by a condensation particle counter (CPC) with a temporally or spatially varying detection threshold diameter. In the preferred embodiment, the sample introduced to the nebulizer may consist of the unaltered source colloid, a colloid downstream of a sample introduction device, or downstream of a colloid concentrator (employing evaporation and/or cross flow filtration).

The basic method of the invention for determining the size distribution of particles in a fluid, involves forming a stream of aerosol droplets of the fluid, the droplets containing particles and dissolved material, evaporating the droplets to generate particles, and measuring the concentration of particles by varying a detection threshold. The basic system or apparatus for determining the size distribution of particles in a fluid, includes a droplet former for forming a stream of aerosol droplets of the fluid, the droplets containing particles and dissolved material, and a condensation particle detector for evaporating the droplets to generate particles and for measuring the concentration of particles, the condensation particle detector having a variable detection threshold.

In one aspect, the invention relates to a condensation particle counter where the degree of supersaturation is temporally varied by adjusting the temperatures of the saturated aerosol stream and/or the walls of the transport cavities on the condensing region. These temperatures may either be adjusted in a stepwise manner or continuously ramped.

In another aspect, the invention relates to a condensation particle counter where the degree of supersaturation is temporally varied by adjusting the ratio of a vapor saturated flow to a dry flow.

In another aspect, the invention relates to a condensation particle counter where the degree of supersaturation is temporally varied by adjusting the vapor content by controlling the mass of vapor delivered to the gas either by adding a controlled amount of liquid to the gas stream or by controlling the exposure of the gas stream to the working fluid surface.

In another aspect, the invention relates to a condensation particle counter where the degree of supersaturation is spatially varied where particles are exposed to an increasing degree of supersaturation. Larger particles (where the onset of condensational growth occurs at a lower supersaturation) have a longer growth period and thus the resulting droplets are larger. By measuring the amount of light scattered by these droplets (larger droplets lead to more scattered light), the size of the original particle can be inferred.

The present invention is believed to involve novel elements, combined in novel ways to yield more than predictable results. The problems solved by the invention were not fully recognized in the prior art.

The aspects, features, advantages, benefits and objects of the invention will become clear to those skilled in the art by reference to the following description, drawings and claims.

DETAILED DESCRIPTION

The present invention describes a method for determining the size distribution of particles within a colloid. This is achieved by nebulization of the colloid where upon evaporation of the nebulized droplets, the resulting aerosol consists of particles previously present in the colloid now suspended in a background gas. In the particle sizes of interest, these particles are not detectable by optical means. The concentration of these particles is then measured using a condensation particle counter with a varying minimum detected particle size.

Figure 1:
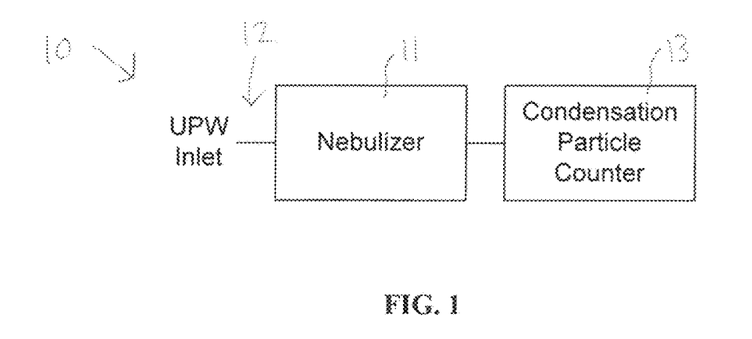
FIG. 1 is a schematic representation of a preferred embodiment of the system with no upstream colloid modification.

FIG. 1, is a simplified diagram of a first embodiment of the system 10 of the invention. The system 10 includes a nebulizer 11 having an input 12. The nebulizer 11 forms droplets. A condensation particle counter or detector 13 is communicatively connected to the nebulizer 11. In this embodiment of the system 10, the water sample is unaltered. This configuration is most useful for monitoring ultrapure water systems for particles. This configuration is also beneficial for testing size dependent particle breakthrough for water filters (where a colloid is introduced upstream of the filter).

Figure 2:
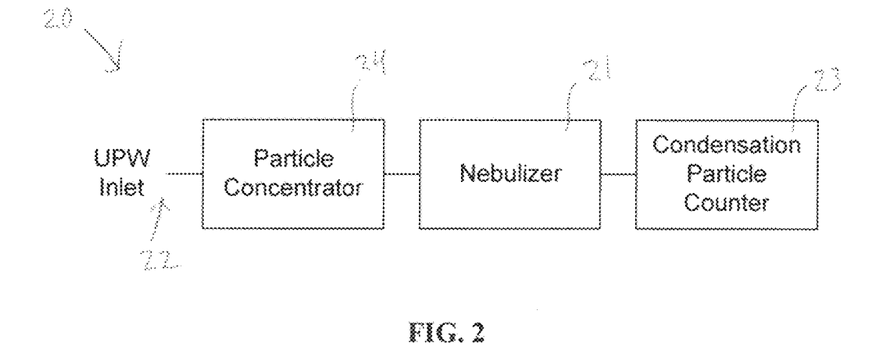
FIG. 2 is a schematic representation of an embodiment of the system employing a particle concentrator.

In FIG. 2, an alternative embodiment of the system 20 is shown diagrammatically and having a nebulizer 21 and condensation particle detector 31. A particle concentrator 24, with input 22, is connected to the nebulizer 21. The sample is modified by concentrating the particles within the colloid. This configuration results in reduced statistical error for low concentrations by increasing the effective sampled volume. Methods for concentration include, but are not limited to, solvent evaporation and cross flow filtration.

Figure 3:
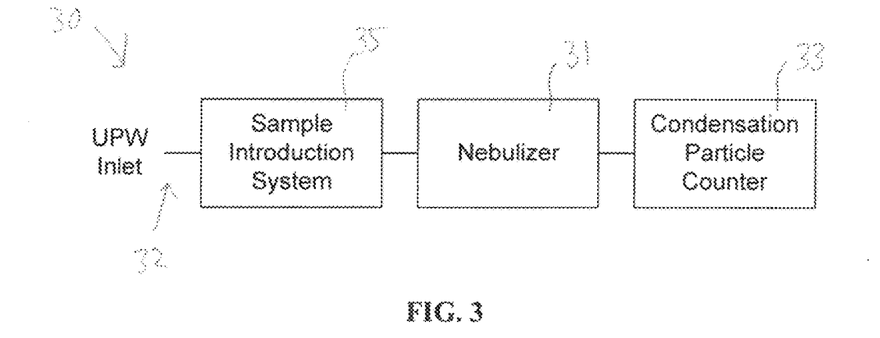
FIG. 3 is a schematic representation of an embodiment of the system employing a colloid or solute introduction device.

Referring to FIG. 3, a further embodiment of the system 30 is shown diagrammatically including a nebulizer 31 and condensation particle counter 33. A sample introduction system 35, including inlet 32, is connected to the nebulizer 31. In this embodiment of the system 30, the sample is modified by injecting a higher concentration colloid into a clean solvent stream. This technique is useful for characterizing the particle size distribution of the high concentration colloid but more importantly it is required to calibrate the inspected volume of the nebulizer device by using a colloid of known concentration.

Figure 4:
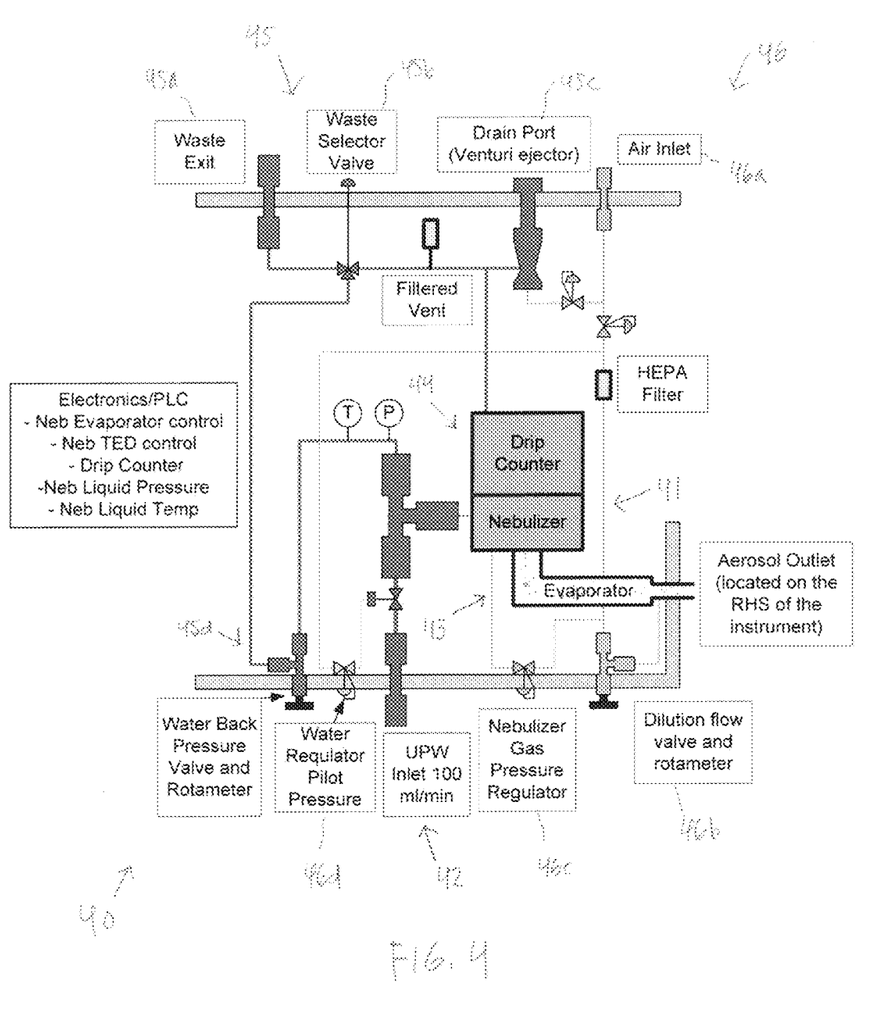
FIG. 4 is a schematic representation of a preferred embodiment of the nebulizer system of the invention.
Figures 5A, 5B, 5C:
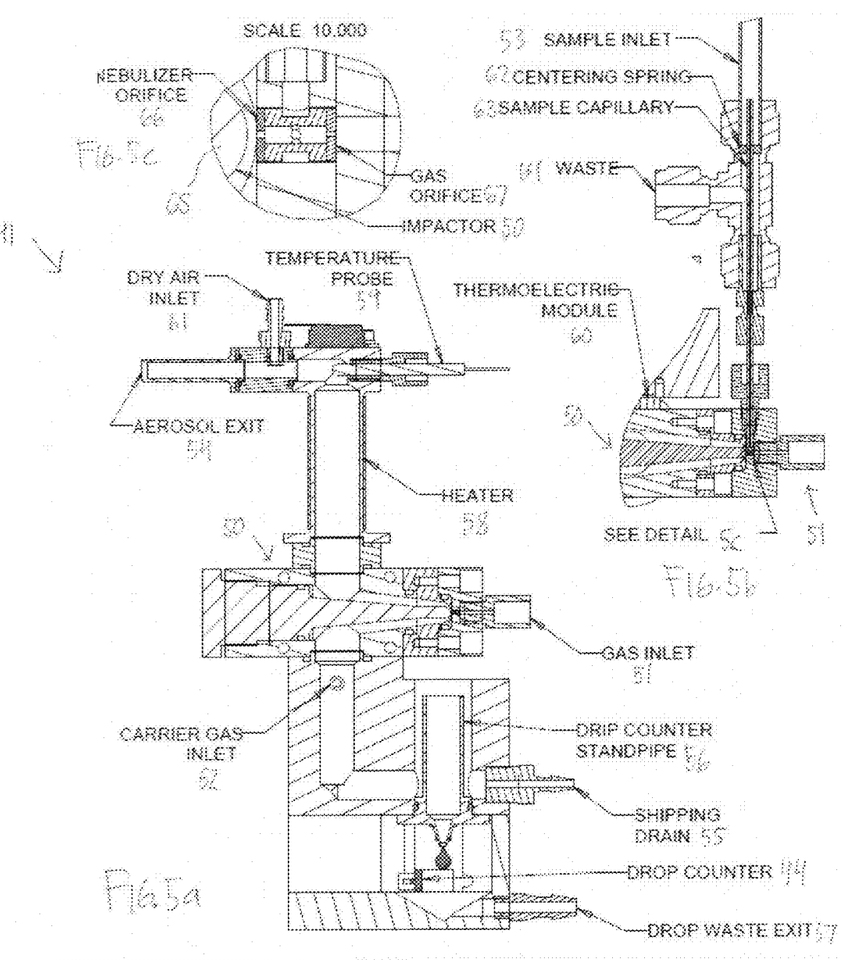
FIGS. 5a-c shows cross sectional views of the nebulizer.

FIGS. 4-5 illustrate a preferred embodiment of the nebulizer and associated components 40 utilized in the systems 10, 20 and 30. Referring first to FIG. 4, the nebulizer 41 is communicatively connected to an input inlet assembly 42 and an output evaporator 43. The inlet 42 is for ultrapure water (UPW). The evaporator 43 has an aerosol outlet. A drop counter 44 is connected to the nebulizer 41. The system 40 has a drain system 45 is communicatively connected to the water inlet 42 and to the drip counter 44. The embodiment of the drain system 45 preferably includes a waste exit 45a, a selector valve 45b, a drain port 45c and a water back pressure valve and meter 45d. The system 40 also has a gas/air system 46 communicatively connected to the nebulizer 41. The system 46 preferably includes an air inlet 46a, a dilution flow valve and meter 46b, a nebulizer gas pressure regulator 46c, and a water regulator 46d. This system 40 has associated electronics and program logic control for automating function of the evaporator 43, TED control, drip counter 44 and system liquid pressure and temperature.

Referring next to FIGS. 5a and 5b, the nebulizer 41 includes an impactor pin 50, a gas inlet 51, a carrier gas inlet 52, a sample inlet 53 and an aerosol exit 54. The connection of the drop counter 44 is also shown. The drop counter 44 also has a shipping drain 55 drop counter stand pipe 56 and a drop waste exit 57. A heater 58, temperature probe 59 and thermoelectric module 60 are also connected to this assembly 41. A dry air inlet 61 is coupled proximate the aerosol exit 54. The sample inlet 53 arrangement preferably includes a centering spring 62, sample capillary 62 and waste 64 connection. FIG. 5c shows the arrangement of the tip 65 of the impactor 50 relative to a nebulizer orifice 66 and gas orifice 67.

Figure 6:
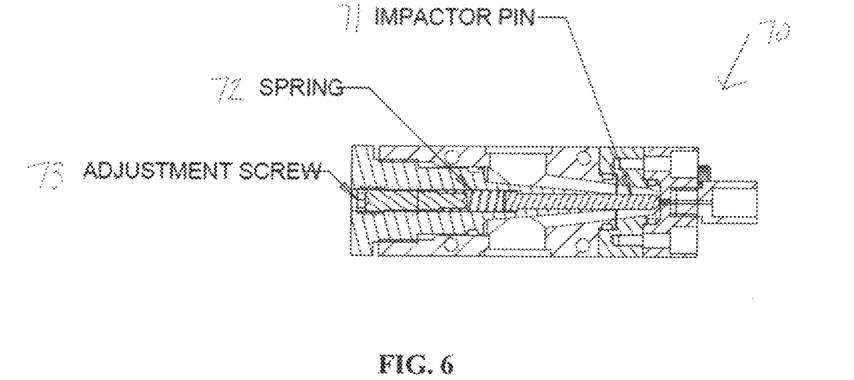
FIG. 6 illustrates an embodiment of the movable impactor pin.

Referring to FIG. 6, a preferred embodiment of the nebulizer incorporates a movable, spring loaded impactor pin assembly 70 including a pin 71, a spring 72 and an adjustment screw 73. The movable pin 70 provides two advantages; the first is to minimize the potential for damage done by the pin to orifices and mounting surfaces during adjustments. The second is that the position of the pin will vary with the stagnation pressure of the gas stream exiting the secondary nebulizer orifice. This results in less variation in the performance of the impactor due to thermal expansion induced geometric changes and/or liquid and gas pressures.

Alternative embodiments of the droplet forming element or nebulizer that are useable with the system of the invention are shown and described in U.S. Pat. No. 7,852,465 entitled System For Measuring Liquid Flow Rates issued to Blackford et al. on Dec. 14, 2010; U.S. Pat. No. 8,272,253 entitled Particle Concentration Measurement Technology issued to Grant et al. on Sep. 25, 2012; and U.S. Pat. No. 8,573,034 entitled Residue Concentration Measurement Technology issued to Grant et al. on Nov. 5, 2013. The U.S. Pat. No. 8,272,253 describes particular methods and criteria for aerosolizing a colloid. The disclosures of these US patent documents are hereby incorporated by reference.

One unique feature of the nebulizer of this invention is the recessed location of the nebulization region which allows for large droplets (where the residue after evaporation may approach particle sizes of interest) to gravitationally settle prior to entering the evaporation section.

FIGS. 7-10 show several embodiments of a variable detection limit condensation particle counter of the system of the invention. The condensation particle counters operate on the principle that in a supersaturated vapor, vapor will condense onto particles larger than a critical size. This is referred to as activation or nucleation of the particle. These activated particles then grow by several orders of magnitude making them easily detected using optical means. The degree of supersaturation of a vapor in an aerosol is defined by the saturation ratio:

$$S = p_v/p_{sat},$$

where ($p_v$) is the ratio of vapor pressure of a gas within the aerosol and $p_{sat}$ is the vapor pressure of that same gas over a flat surface of its condensed phase.

The critical particle diameter may be calculated using the Kelvin relation:

$$d_{p,critical} = \frac{k_B T}{4\sigma v_v \ln S},$$

where $k_B$ is Boltzmann's constant. T is the temperature, $\sigma$ is the condensed phase surface tension, and $v_v$ is the volume of a vapor molecule.

The Kelvin relation accounts for the surface tension work upon the addition of a vapor molecule which is non-negligible for highly curved surfaces. The Kelvin relation shows how the minimum detected particle diameter varies with the saturation ratio of the working vapor.

Figure 7:
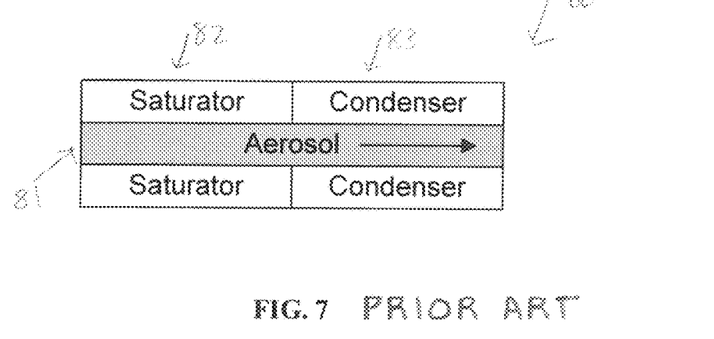
FIG. 7 is a block diagram showing a conventional condensation particle counter (CPC).

FIG. 7 shows a conventional condensation particle counter or detector (CPC) 80 where an aerosol 81 travels through a saturation region 82 which brings the vapor pressure of the working fluid in the aerosol equal to $p_{sat}$ prior to entering the condensation region. In the case where the thermal diffusivity of air is higher than the mass diffusivity of the working vapor, the super-saturated vapor state is created by exposing an aerosol containing the working vapor to relatively cold transport walls. Conversely, where the mass diffusivity of the vapor is higher than the thermal diffusivity of air (e.g. water), the saturated aerosol is exposed to warm wet walls. The saturation ratio for these CPCs is temporally modified by changing the saturator 82 and/or condenser 83 temperatures.

Figure 8:
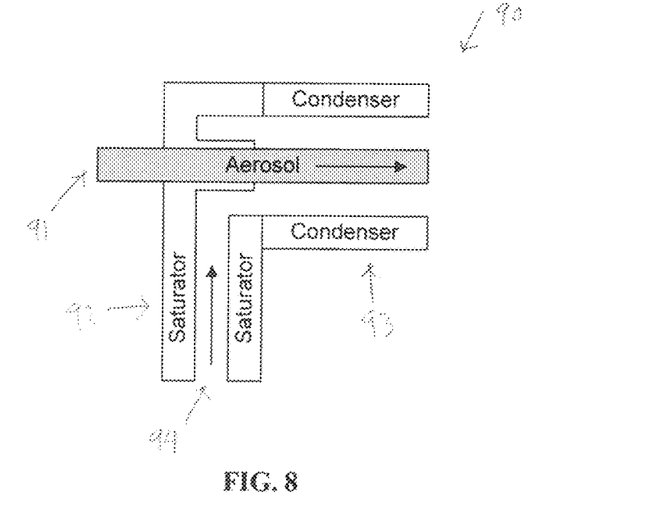
FIG. 8 is a block diagram showing an embodiment of the CPC which utilizes a clean sheathed saturator flow.
Figure 9:
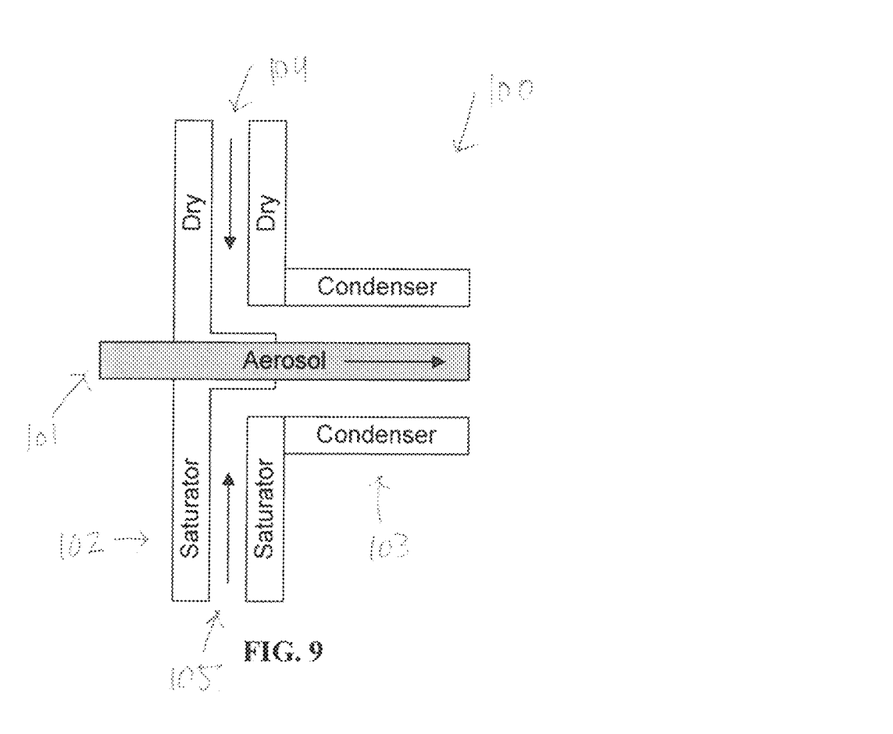
FIG. 9 is a block diagram showing an embodiment of the CPC where the degree of supersaturation is modified by a ratio of dry to vapor laden air streams.
Figure 10:
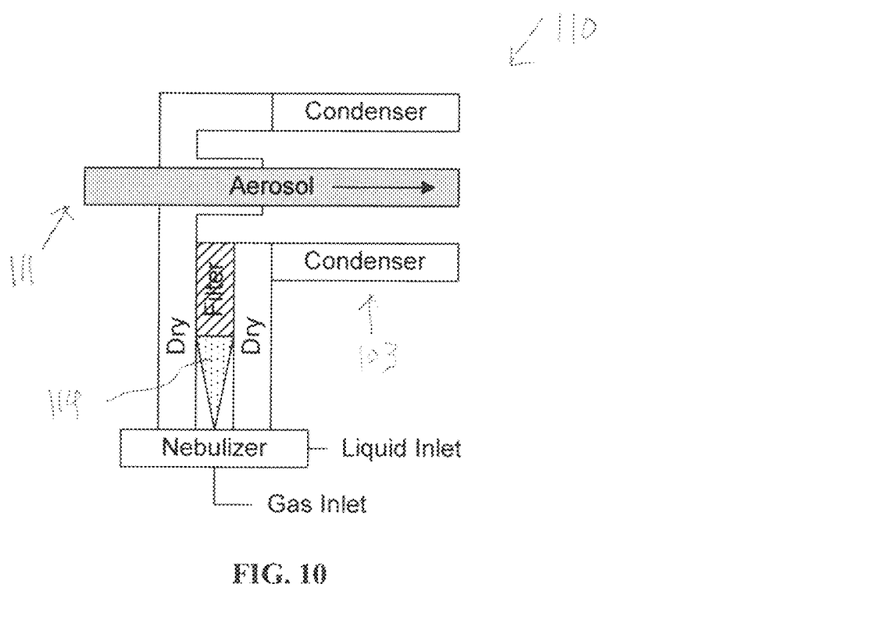
FIG. 10 is a block diagram showing an embodiment of the CPC where the degree of supersaturation is modified by controlling the mass flow of vapor.

An alternative embodiment of a CPC 90 shown in FIG. 8, and having a saturator 92 and condensor 93, sheaths the aerosol flow 91 with particle free gas 94, confining the aerosol to streamlines that experience similar levels of supersaturation resulting in a sharper size 'cutoff'. In these configurations the sheath flow may be pre-loaded with vapor prior to being introduced to the aerosol stream. For pre-loaded sheath flows, the saturation ratio may also be varied by controlling the vapor pressure of the sheath flow to a sub-saturated level. This can be accomplished by varying the ratio of dry 104 to saturated 105 air as shown in the FIG. 9 (including CPC 100 with saturation region 102 and condensor region 103, and aerosol flow 101) or by controlling the mass flow of vapor 114 introduced to the sheath gas as shown in FIG. 10 (CPC 110). In all cases the aerosol may or may not be exposed to the working fluid directly. An additional advantage to controlling the vapor pressure of a condensing vapor is that if two condensing vapors are utilized, the temperature differential required for the onset of condensation for one of the vapors which might otherwise cause homogeneous (self activating) condensation for the second vapor can be mitigated by limiting the vapor content of the second vapor. These 'two vapor' approaches may be used when a specific working vapor is required for condensing onto very small particles (e.g. diethylene glycol) or onto particles with material dependent threshold sizes (e.g. water onto hydrophobic particles) where the initially nucleating vapor does not grow the particles to a sufficient size and the second vapor is needed to 'boost' the particles to a larger size.

For mixing type CPCs, supersaturation is achieved by mixing two gas streams of different temperatures where the hotter stream contains condensing vapor and the colder stream may or may not contain condensing vapor. If the relationship for the working fluid, dPsat/dTemp is positive, then it is possible to achieve an operating condition where the vapor content in the resulting mixture is higher than the saturated vapor content at the mixed gas temperature. The level of supersaturation can be controlled by varying the temperatures of the gas streams, the flow ratio between the gas streams, and/or explicit control of the vapor content using one of the aforementioned methods described for laminar flow CPCs. Note that mixing type CPCs require a growth section (typically cooled walls) downstream of the mixing region.

For temporally varying supersaturation levels, the size distribution of the particles in the colloid may be inferred by differentiating the measured aerosol concentration as a function of threshold diameter. For spatially varying supersaturation levels, the size distribution is inferred directly (See for example, U.S. Pat. No. 7,656,510). Temporal variation may be incremental with non-sampled periods allowing for steady state conditions, or continuous with active control and or monitoring of flows and temperatures to calculate the saturation ratio and ultimately the minimum detected particle size.

The CPC working fluid is ideally inert and non-toxic with a very low surface energy thereby limiting any material dependence for the minimum detected particle size. Fluorinated solvents such as 3M FLUORINERT FC-40 and FC-43 have been used as working fluids but they are expensive and have deleterious environmental effects. 3M NOVEC fluids (7500) have similar properties but are cheaper and have less environmental impact. Any of the above CPCs may use these Fluorinated solvents as the working fluid (or as the primary condensing fluid in a two vapor system), much of the solvent can be recovered from the condensing region in the CPC and a downstream secondary condenser. Due to the low miscibility between the fluorinated solvents and water, the fluorinated solvent can be recycled by drawing off of the appropriate strata within the condensed fluid reservoir.

Figure 11:
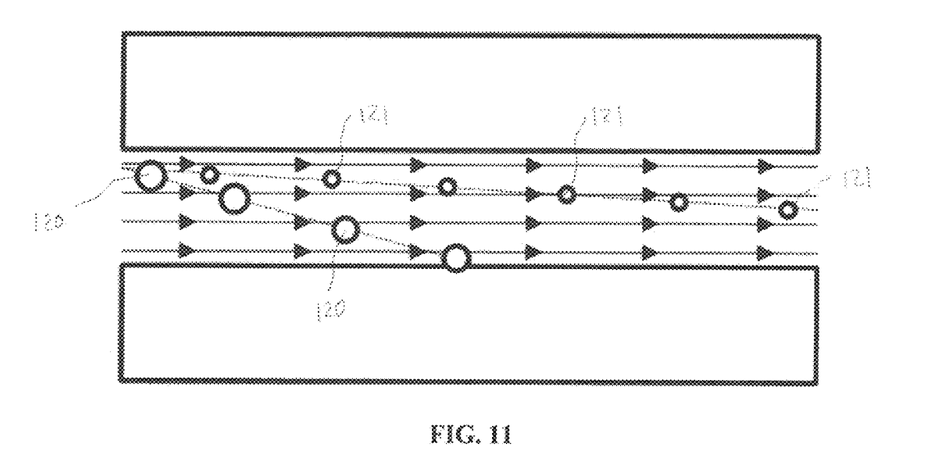
FIG. 11 is a diagram illustrating gravitational settling of large droplets.

Another embodiment of this invention utilizes an alternate large droplet removal mechanism which may be used in tandem with the existing nebulizer impactor pin described in the text. Additionally, an alternate large droplet removal mechanism may be used in place of the previously described impactor pin. Specifically, the additional large droplet removal mechanisms operate by either gravitational settling or by inertial driven capture. Referring to FIG. 11, for gravitational settling, large droplets 120 will precipitate from an aerosol at a higher rate than smaller droplets 121. The terminal velocity of particles in the size range of interest can be calculated using:

$$V_{settling} = 3E{-}8 * \rho_p d_p^2$$

where $\rho_p$ is in kg/m³ and $d_p$ is in μm

Figure 12:
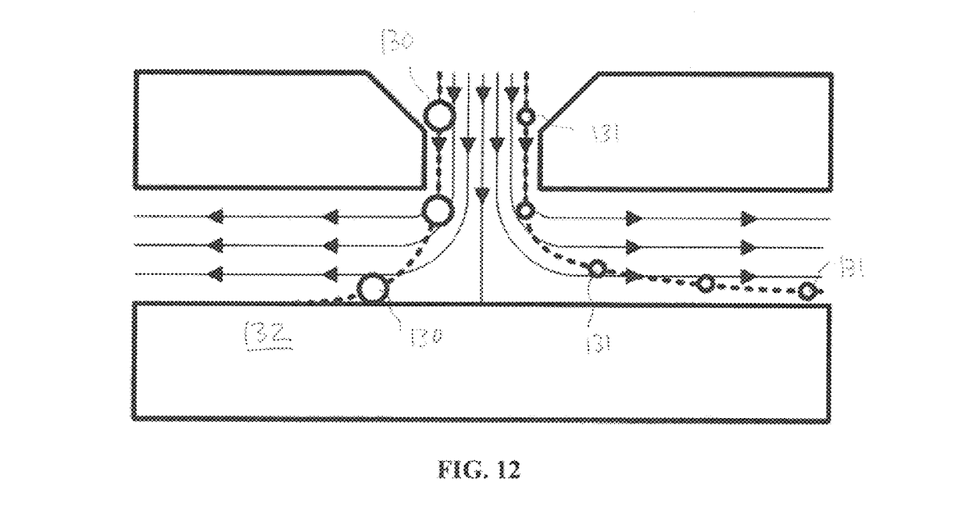
FIG. 12 is a diagram illustrating inertial impaction.

Therefore, with sufficient residence time tbr a given settling distance, large droplets will be preferentially removed from the aerosol. This may be accomplished by either a long tube or by parallel plates. Referring to FIG. 12, inertial driven capture operates on the principle that larger droplets 130 will have a higher tendency to cross flow streamlines (increased ratio of inertia to drag forces) compared to smaller droplets 131. This phenomenon is used advantageously to separate larger droplets 130 from smaller ones 131 either by capture on a surface as is the case with traditional impactors or into a secondary flow as is the case with virtual impactors. Large droplets 130 carry more momentum causing them to cross more streamlines, thus causing them to impact on an opposing surface 132. Smaller droplets 131 are able to change direction more rapidly and are therefore able to escape the impaction region. For round jet impactors, the particle diameter at which 50% of the particles are removed from the aerosol ($d_{50}$) can be calculated using $$d_{50} = \sqrt{\frac{9\mu\pi D^3 (Stk_{50,Round})}{4\rho Q}},$$

where $\mu$ is the gas viscosity, D is the jet diameter, $\rho$ is the particle density, and Q is the volumetric gas flow rate (Marple et al. Atmospheric Environment Vol. 10, pp. 891-896) for round jet impactors, $Stk_{50}$ is around 0.24.

Droplets that are on streamlines near the boundary layer achieve a lower velocity and therefore have less momentum which causes a bias towards large droplets escaping the impactor. Large droplet removal efficiency can be improved by adding a annular sheathing flow to the aerosol which contines the aerosol 'jet' in the centerline of the flow ensuring that all of the droplets are at a sufficient velocity to be removed.

Figures 13A, 13B:
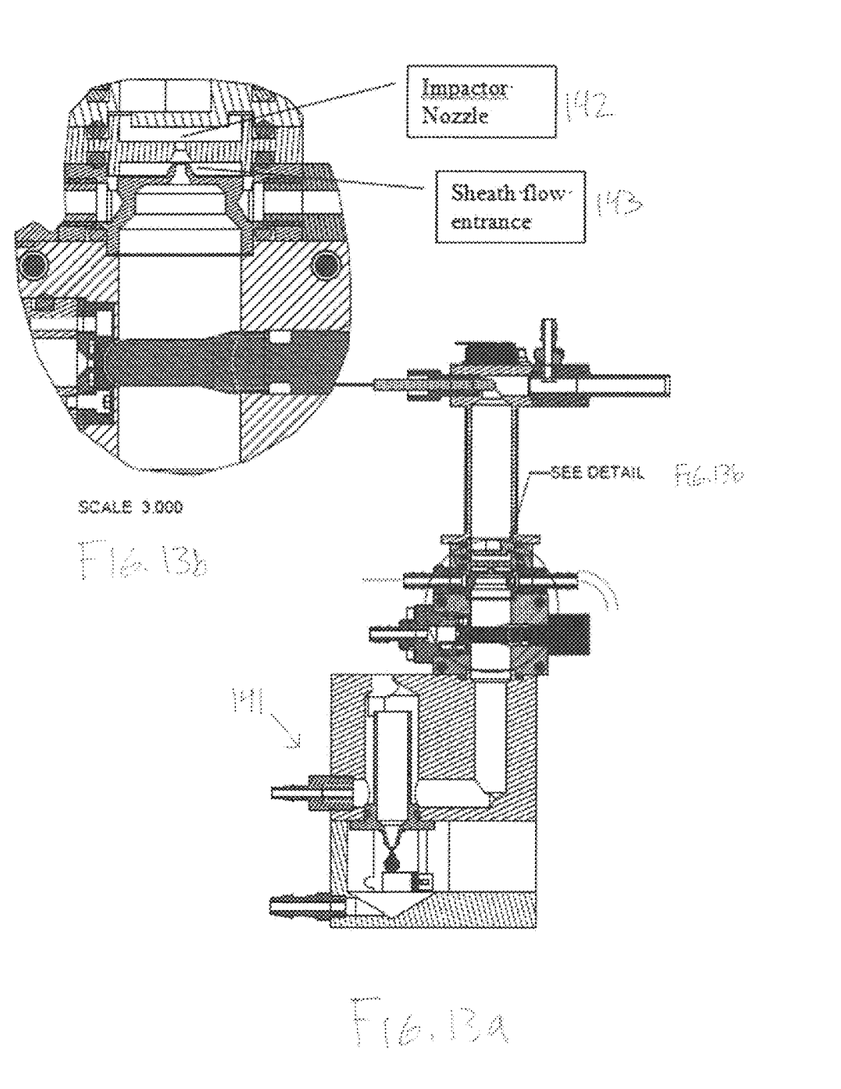
FIGS. 13a and 13b show an embodiment of a jet impactor nebulizer with large droplet removal functionality.
Figure 14:
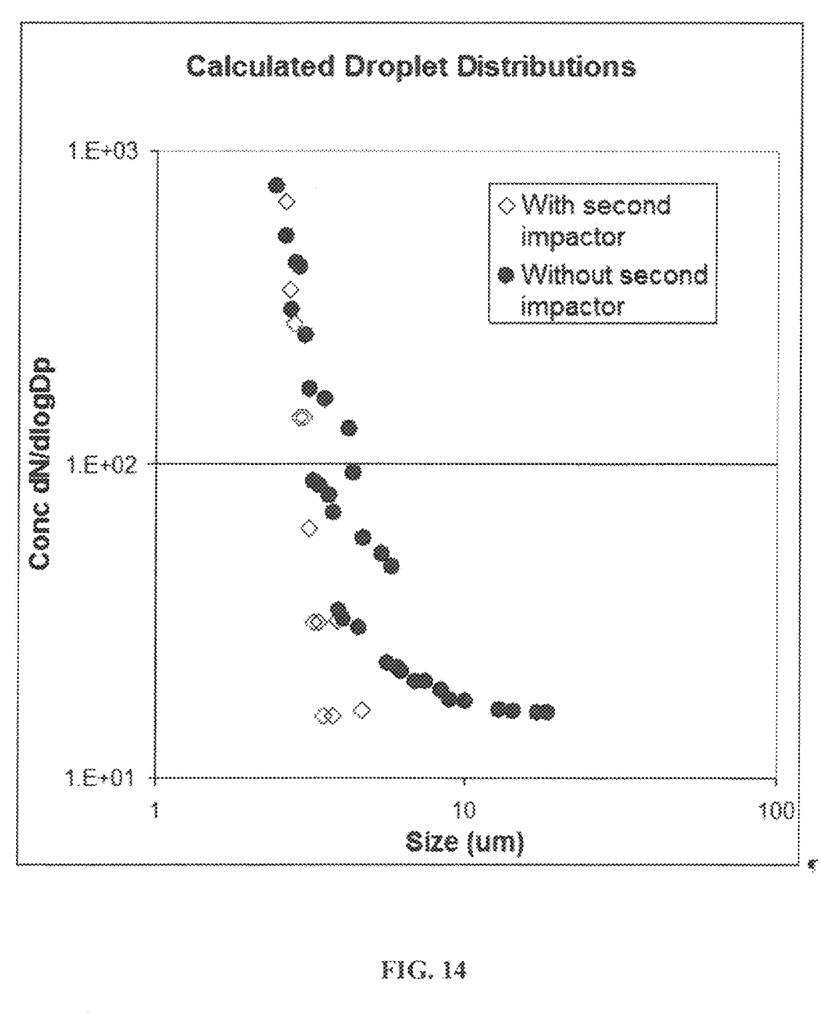
FIG. 14 is graph showing the expected reduced maximum nonvolatile residues particle sizes resulting from large droplet removal.

FIGS. 13 *a-b* show an embodiment of a nebulizer 140 including a large droplet removal means. The assembly includes a jet impactor 141, sheath flow entrance 142 and an impactor nozzle 143. The impacting surface is heated to remove, by evaporation, the liquid introduced by impacted droplets. Data showing enhanced large droplet removal by the jet impactor is shown in FIG. 14, a graph of calculated droplet distributions.

A basic embodiment of the method of the present invention comprises the step of creating fine droplets of the fluid (nebulization) containing particles and dissolved material at concentrations equal to the bulk material. Upon evaporation of the liquid, the gas-borne droplet becomes either a particle consisting of non-volatile dissolved material or a particle consisting of a colloid particle and non-volatile dissolved material. The particles are then sampled by a condensation particle counter (CPC) with a temporally or spatially varying detection threshold diameter. In the preferred embodiment, the sample introduced to the nebulizer may consist of the unaltered source colloid, a colloid downstream of a sample introduction device, or downstream of a colloid concentrator (employing evaporation and/or cross flow filtration). In one embodiment, the degree of supersaturation is temporally varied by adjusting the temperatures of the saturated aerosol stream and/or the walls of the transport cavities on the condensing region. These temperatures may either be adjusted in a stepwise manner or continuously ramped. In another embodiment, the degree of supersaturation is temporally varied by adjusting the ratio of a vapor saturated flow to a dry flow. In another embodiment, the degree of supersaturation is temporally varied by adjusting the vapor content by controlling the mass of vapor delivered to the gas either by adding a controlled amount of liquid to the gas stream or by controlling the exposure of the gas stream to the working fluid surface. And in yet another embodiment, the degree of supersaturation is spatially varied where particles are exposed to an increasing degree of supersaturation. Larger particles (where the onset of condensational growth occurs at a lower supersaturation) have a longer growth period and thus the resulting droplets are larger. By measuring the amount of light scattered by these droplets (larger droplets lead to more scattered light), the size of the original particle can be inferred.

Other embodiments of the method of the invention include, but are not limited to, the following Examples. A base process is for determining the size distribution of particles in a colloid by measuring the size distribution of aerosolized particles using an aerosol particle detector with a variable detection threshold. Particular methods and criteria for aerosolizing the colloid are described in incorporated by reference U.S. Pat. No. 8,272,253. One version of the process involves using a thermally diffusive laminar flow type condensation particle detector.

A. In one route, the detection limit is varied by adjusting the condenser temperature downstream of an aerosol flow saturated with the working vapor, and:
  i. the temperature is adjusted in a stepwise manner and the concentration measurement is made after reaching steady state; or
  ii. alternatively, the temperature is adjusted and measured throughput the transition period where the detection limit is inferred from the measured temperatures;

B. In another route, the detection limit is varied by adjusting the temperature of the vapor saturated aerosol, and:
  i. the temperature is adjusted in a stepwise manner and the measurement is made after reaching steady state, or
  ii. alternatively, the temperature is adjusted and measured throughput the transition period where the detection limit is inferred from the measured temperatures, C. In a further route, the detection limit is varied by adjusting the temperature of the vapor saturated aerosol and the temperature of the walls in the condenser region, and:
  i. the temperature difference between the saturator and condenser is adjusted in a stepwise manner and the measurement is made after reaching steady state, or
  ii. alternatively, the temperature difference between the saturator and condenser is adjusted and measured throughput the transition period where the detection limit is inferred from the measured temperatures.

D. In yet another route, the detection limit is adjusted by varying the condensing vapor content prior to the condenser, and
  a. the aerosol is split between a dry passage and a saturating passage using, for example, a proportional three way valve, or
  b. alternatively, the aerosol is coaxially sheathed by clean air where the vapor content in the sheath air is adjusted to a controlled vapor pressure by varying the ratio of dry and saturated gas streams supplying the sheath flow (note the dry stream may be omitted):
    i. the aerosol flow does not contain vapor,
    ii. alternatively, the aerosol flow is saturated with vapor, or
    iii alternatively the ratio of the aerosol to sheath flow is varied to control the vapor pressure of the resulting mixture.

Another version of the process involves using a mixing type condensation particle detector.
 a. where the aerosol may be present in either or both of the mixing gas streams, and
 b. the detection threshold is varied by adjusting the temperature difference between the hot and cold mixing flows:
  i. where the temperature is adjusted in a stepwise manner and the concentration measurement is made after reaching steady state, or
  ii. where the temperature is adjusted and measured throughput the transition period where the detection limit is inferred from the measured temperatures.

Also using mixing type condensation particle detector:
 a. the aerosol may be present in either or both of the mixing gas streams, and
 b. the detection threshold is varied by adjusting the working vapor content in the hot and/or cold flows:
  i. the vapor pressure is controlled by a metered liquid introduction such as a syringe or peristaltic pump driven nebulizer,
  ii. alternatively, the vapor pressure is controlled by limiting the exposure of the gas stream to the surface of the saturating liquid either spatially or temporally, or iii. as a further alternative, the vapor pressure is controlled by varying the ratio of dry and saturated gas streams in either the hot or cold flows.

Again using the mixing type condensation particle detector:

a. where the aerosol may be present in either or both of the mixing gas streams, and b. where the detection threshold is varied by adjusting the flow ratio of hot and cold gas streams:

i. where vapor is present in both gas streams, or ii. where vapor is present only in the hot gas stream.

Returning to the thermally diffusive laminar flow type condensation particle detector, in another embodiment of method, the temperature of the condenser region may be spatially varied resulting in smaller particles experiencing less time for growth where the initial particle size may be inferred from the size of the resulting droplets.

In a further aspect of the method, where with either a laminar flow or mixing type a condensation particle counter, the process involves controlling the vapor pressure of one or more condensing fluids by explicitly controlling the mass of vapor present in the aerosol prior to the condensing region:

a. the controlled vapor is the only condensing vapor:

i. the vapor pressure is controlled by a metered liquid introduction such as a syringe or peristaltic pump driven nebulizer, or ii. alternatively, the vapor pressure is controlled by limiting the exposure of the gas stream to the surface of the saturating liquid either spatially or temporally; or b. alternatively, where two vapors are present:

i. one vapor is saturated but alone is not suitable for sufficient particle growth (e.g. diethylene glycol) and the controlled vapor is present to continue growth to a sufficient size (e.g. butanol), wherein the growth vapor would otherwise undergo homogeneous nucleation at the temperatures required for nucleation using the saturated vapor, or ii. alternatively, the secondary vapor concentration is controlled by varying the ratio of gas saturated with the primary vapor and gas saturated with the primary and secondary vapors.

The above methods may be practiced by calculating the differential concentration measured by the CPC at each of the operating condition. The colloidal particle size distribution may be inferred directly by the condensed droplet size distribution. The process may be used to measure the particle size distribution of an unaltered colloid, a diluted colloid, or a colloid passing through a colloid concentrator. Colloid concentration may be accomplished operates using cross flow filtration or by evaporation. Examples of evaporative methods include a semi porous membrane e.g. Porous PTFE (Zeus Corp) bathed in hot, dry gas, or by exposing the liquid surface to hot, dry gas. A preferred condensing vapor is a Fluorinated Solvent (Fluorinert or Novec). In this case, the condensing vapor is preferably recovered by condensation. The condensed working fluid is not miscible with the colloid solvent. And, the recovered working fluid is recycled by drawing it from the appropriate strata within the recovered liquids.

Regarding the method of using a movable impactor pin where an axial force is applied to the pin, the force may be constant (e.g. provided by a regulated gas source), the force may vary with pin position (e.g. provided by a spring), or the force may be adjustable (e.g. by adjusting the preload of a spring, or adjustment by changing gas pressure).

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A method of determining the size distribution of particles in a fluid, comprising the steps of forming a stream of aerosol droplets of the fluid, the droplets containing particles and dissolved material, evaporating the droplets to generate particles, and measuring the concentration of particles by varying a detection threshold, wherein the steps of evaporating droplets and measuring concentration are accomplished by condensation particle counting, wherein condensation particle counting involves saturating the droplets and condensing the droplets, and wherein the degree of saturation is varied, and wherein condensation particle counting is accomplished by thermally diffusive laminar flow type condensation having a gas flow stream saturated with droplets, an upstream saturation region, a downstream condensing region.

2. The method of claim 1, wherein fluid is colloid.

3. The method of claim 2, wherein the colloid is an unaltered source colloid.

4. The method of claim 2, wherein the size distribution of particles in the colloid is determined downstream of a sample introduction device.

5. The method of claim 2, wherein the size distribution of particles in the colloid is determined downstream of a colloid concentrator.

6. The method of claim 5, wherein the colloid is concentrated by evaporation.

7. The method of claim 5, wherein the colloid is concentrated by cross flow filtration.

8. The method of claim 1, wherein step of forming is accomplished by nebulization.

9. The method of claim 1, wherein the step of evaporating generates a particle consisting of a non-volatile dissolved material or a particle consisting of a colloid particle and non-volatile dissolved material.

10. The method of claim 1, wherein the detection threshold is a diameter.

11. The method of claim 1, wherein the detection threshold is varied temporally.

12. The method of claim 11, wherein temporally varying the detection threshold involves varying temperature.

13. The method of claim 12, wherein the temperature of the saturated droplets is varied.

14. The method of claim 12, wherein the temperature of a condenser is varied.

15. The method of claim 12, wherein temperature is varied stepwise.

16. The method of claim 12, wherein temperature is varied continuously ramped.

17. The method of claim 11, wherein temporally varying the detection threshold involves varying the ratio of a flow of vapor saturated with droplets with a separate flow of a dry gas.

18. The method of claim 11, wherein temporally varying the detection threshold involves varying the mass of vapor delivered to a flow of gas.

19. The method of claim 18, wherein the mass of vapor delivered is varied by adding a controlled amount of liquid to a gas stream.

20. The method of claim 18, wherein the mass of vapor delivered is varied by controlling the exposure of a gas stream to a working fluid surface.

21. The method of claim 1, wherein the detection threshold is varied spatially.

22. The method of claim 21, wherein the degree of supersaturation is increased and further comprising the steps of (1) measuring the amount of light scattered by droplets, and (2) inferring the size of the particles in the droplet by the amount of light scattered wherein particle size is directly proportional to the amount of light scattered.

23. The method of claim 1, wherein the detection threshold is varied by varying the temperature of the condensing region.

24. The method of claim 23, wherein the temperature is varied stepwise, and the concentration measurement is made after reaching a steady state.

25. The method of claim 23, wherein the temperature is varied continuously throughout a transition period, and a detection threshold is inferred from measured temperatures.

26. The method of claim 1, wherein the detection threshold is varied by varying the temperature of the gas flow stream saturated with droplets.

27. The method of claim 26, wherein the temperature is varied stepwise, and the concentration measurement is made after reaching a steady state.

28. The method of claim 26, wherein the temperature is varied continuously throughout a transition period, and a detection threshold is inferred from measured temperatures.

29. The method of claim 1, wherein the detection threshold is varied by varying the temperature of the gas flow stream saturated with droplets and the temperature of the condensing region.

30. The method of claim 29, wherein the temperature difference between the saturation region and the condensing region is varied stepwise, and the concentration measurement is made after reaching a steady state.

31. The method of claim 29, wherein the temperature difference between the saturation region and the condensing region is varied continuously throughout a transition period, and a detection threshold is inferred from measured temperatures.

32. The method of claim 1, wherein the detection threshold is varied by varying the gas flow stream saturated with droplets prior to the condensing region.

33. The method of claim 32, ratio of the gas flow stream saturated with droplets to separate gas flow stream of a dry gas.

34. The method of claim 32, wherein the gas flow stream to be saturated with droplets is coaxially sheathed with a clean, sheath air, and wherein the vapor content of the sheath air is adjusted to a predetermined vapor pressure by varying the ratio of dry air and saturated gas.

35. The method of claim 34, wherein the gas flow stream does not contain vapor.

36. The method of claim 34, wherein the gas flow stream is saturated with vapor.

37. The method of claim 34, wherein the ratio of gas flow stream to sheath air is varied to control the vapor pressure of the resulting mixture.

38. The method of claim 1 wherein the temperature of the condensing region is spatially varied, and wherein particle size is inferred from size of the resulting droplets, particle size being directly proportional to droplet size.

* * * * *